United States Patent
Barty et al.

(10) Patent No.: US 7,564,241 B2
(45) Date of Patent: Jul. 21, 2009

(54) ISOTOPIC IMAGING VIA NUCLEAR RESONANCE FLUORESCENCE WITH LASER-BASED THOMSON RADIATION

(75) Inventors: Christopher P. J. Barty, Hayward, CA (US); Frederic V. Hartemann, San Ramon, CA (US); Dennis P. McNabb, Alameda, CA (US); Jason A. Pruet, Brentwood, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 40 days.

(21) Appl. No.: 11/528,182

(22) Filed: Sep. 26, 2006

(65) Prior Publication Data

US 2009/0147920 A1    Jun. 11, 2009

Related U.S. Application Data

(60) Provisional application No. 60/720,965, filed on Sep. 26, 2005.

(51) Int. Cl.
*G01V 3/00* (2006.01)
(52) U.S. Cl. .......................... 324/304; 378/57
(58) Field of Classification Search ................. 324/304; 378/57
See application file for complete search history.

(56) References Cited

U.S. PATENT DOCUMENTS

| | | | |
|---|---|---|---|
| 3,780,294 A | 12/1973 | Sowerby | |
| 5,040,200 A * | 8/1991 | Ettinger et al. | ................. 378/88 |
| 5,115,459 A | 5/1992 | Bertozzi | |
| 5,293,414 A * | 3/1994 | Ettinger et al. | ................. 378/88 |
| 5,323,004 A | 6/1994 | Ettinger et al. | |
| 5,420,905 A | 5/1995 | Bertozzi | |
| 6,442,233 B1 * | 8/2002 | Grodzins et al. | ............... 378/57 |
| 6,661,818 B1 | 12/2003 | Feldman et al. | |
| 6,684,010 B1 | 1/2004 | Morris et al. | |
| 7,060,983 B2 * | 6/2006 | Turner | ................... 250/370.09 |
| 7,120,226 B2 * | 10/2006 | Ledoux et al. | ................. 378/57 |

(Continued)

FOREIGN PATENT DOCUMENTS

WO    WO 2005/081017 A1    9/2005

*Primary Examiner*—Brij B. Shrivastav
*Assistant Examiner*—Megann E Vaughn
(74) *Attorney, Agent, or Firm*—Michael C. Staggs; John P. Wooldridge; John H. Lee

(57) ABSTRACT

The present invention utilizes novel laser-based, high-brightness, high-spatial-resolution, pencil-beam sources of spectrally pure hard x-ray and gamma-ray radiation to induce resonant scattering in specific nuclei, i.e., nuclear resonance fluorescence. By monitoring such fluorescence as a function of beam position, it is possible to image in either two dimensions or three dimensions, the position and concentration of individual isotopes in a specific material configuration. Such methods of the present invention material identification, spatial resolution of material location and ability to locate and identify materials shielded by other materials, such as, for example, behind a lead wall. The foundation of the present invention is the generation of quasimonochromatic high-energy x-ray (100's of keV) and gamma-ray (greater than about 1 MeV) radiation via the collision of intense laser pulses from relativistic electrons. Such a process as utilized herein, i.e., Thomson scattering or inverse-Compton scattering, produces beams having diameters from about 1 micron to about 100 microns of high-energy photons with a bandwidth of $\Delta E/E$ of approximately $10E^{-3}$.

21 Claims, 6 Drawing Sheets

U.S. PATENT DOCUMENTS

| | | |
|---|---|---|
| 2004/0109532 A1 | 6/2004 | Ford |
| 2005/0179911 A1 | 8/2005 | Boomgarden et al. |
| 2006/0166144 A1 | 7/2006 | Te Kolste et al. |
| 2006/0188060 A1* | 8/2006 | Bertozzi et al. ............... 378/57 |
| 2006/0193433 A1* | 8/2006 | Ledoux et al. ................ 378/57 |
| 2007/0263767 A1* | 11/2007 | Brondo, Jr. .................. 378/57 |

* cited by examiner

Fig. 6(b) NRF

ISOTOPIC IMAGING VIA NUCLEAR RESONANCE FLUORESCENCE WITH LASER-BASED THOMSON RADIATION

RELATED APPLICATION

This application claims priority from U.S. Provisional Patent Application No. 60/720,965, entitled "ISOTOPIC IMAGING VIA NUCLEAR RESONANCE FLUORESCENCE WITH LASER-BASED THOMSON RADIATION," filed on Sep. 26, 2005, and is incorporated by reference in its entirety.

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to detection and imaging of elements using resonance fluorescence and more particularly to a novel nuclear resonance fluorescence system and a method for imaging and detection of desired elements using laser-based Thomson radiation.

2. Description of Related Art

Resonance fluorescence is associated with the high probability for a nucleus to be excited by a photon if the photon energy is slightly greater than the energy of one of the levels of the nucleus. If the excited nucleus decays by the re-emission of the photon, the process is usually referred to as resonance scattering.

A variety of nuclear resonance fluorescence methods that involve shifting and/or broadening the emission line have been suggested to achieve the resonance condition. These methods utilize either mechanical motion, thermal agitation, recoil velocity from a previous radioactive decay, and recoil velocity from a nuclear reaction of a continuous γ-ray spectrum (e.g. Bremsstrahlung).

Background information on a Bremsstrahlung radiation method and apparatus to induce such resonance fluorescence is described in U.S. Pat. No. 5,115,459 A, entitled "Explosives Detection Using Resonance Fluorescence of Bremsstrahlung Radiation," to Bertozzi, patented May 19, 1992, including the following: "The method of the present invention exploits the resonant scattering of photons by nuclei. It involves resonantly exciting the nuclei of a target, a suitcase for example, with a bremsstrahlung photon beam incident on the target. In one embodiment, the subject of copending U.S. application Ser. No. 07/567,970, the energies of the photons scattered directly from the target are measured. The energies of the scattered photons are characteristic of the spacings between the quantized energy state of each nuclear species comprising the target. For example, oxygen has a discrete energy level at 6.92 MeV of excitation characterized by even parity and two units of angular momentum. A bremsstrahlung beam incident on a target with oxygen will excite some of the nuclei to this state. The state will subsequently decay with a lifetime of about $6.8 \times 10^{-15}$ seconds by emitting a photon with an energy of 6.92 Mev."

SUMMARY OF THE INVENTION

Accordingly, the present invention provides a Nuclear Resonance Fluorescence detection method that includes: directing a beam of Thomson radiation comprising a fractional bandwidth of about $10^{-3}$ at a target region so as to probe for one or more suspect materials; resonantly exciting nuclei of the one or more suspect materials within the target region with the beam of Thomson radiation; resonantly exciting nuclei of a reference scatterer with the beam transmitted through the suspect material, wherein the reference scatterer includes one or more predetermined nuclear species of interest; and measuring an energy spectrum of photons resulting from the resonantly excited reference scatterer, wherein a disparity between the attenuation measured for resonant and non-resonant photons indicates a detected suspect material.

Another aspect of the present invention provides for a Nuclear Resonance Fluorescence apparatus that includes a Thomson radiation source configured with a fractional bandwidth of about $10^{-3}$, wherein a measured energy spectrum of photons resulting from a resonantly excited reference scatterer can indicate a detected suspect material.

Accordingly, the present invention entails a novel method and apparatus so as to enable a radiographer to distinguish, for example, isotopic composition of materials, such as, $^{235}U$ from $^{238}U$ or from $^{239}Pu$, or look at isotope variations across interfaces wherein two different materials have been bonded or welded together. Moreover, the intense mono-energetic MeV-scale photon source of the present invention which is configured with about a 1 micron to about a 100 micron spot size, more often about a 10-micron spot size, improves conventional radiography by reducing artifacts from Compton scattering and by improving spatial resolution. Such novel embodiments open the door to observing aging trends over shorter timescales when changes might otherwise be obscured by the noise inherent in current radiographic techniques.

Another capability of the present invention is to obtain high-resolution images of less dense objects located inside a dense object. For example, 7-Lithium, having one of the largest NRF cross-sections known can be exploited in some instances by employing NRF-imaging as disclosed herein using a narrow-band x-ray beam matched to the NRF line in the low-Z object. Other applications include, but are not limited to, dynamic probing of dense, energetic systems, isotope-specific stockpile tomography, picosecond pulsed-positron probes of dynamic metrology, medical imaging of tagged agents, non-destructive inspection of mechanical components, in-situ metrology of crack formation for the aerospace industry, gamma-ray detector characterization and nuclear structure.

BRIEF DESCRIPTION OF THE DRAWINGS

The accompanying drawings, which are incorporated into and form a part of the disclosure, illustrate an embodiment of the invention and, together with the description, serve to explain the principles of the invention.

FIG. 6(b) shows imaging of a light object enclosed in a container using Nuclear Resonance Fluorescence radiography of the present invention.

DETAILED DESCRIPTION OF THE INVENTION

Figure 1:
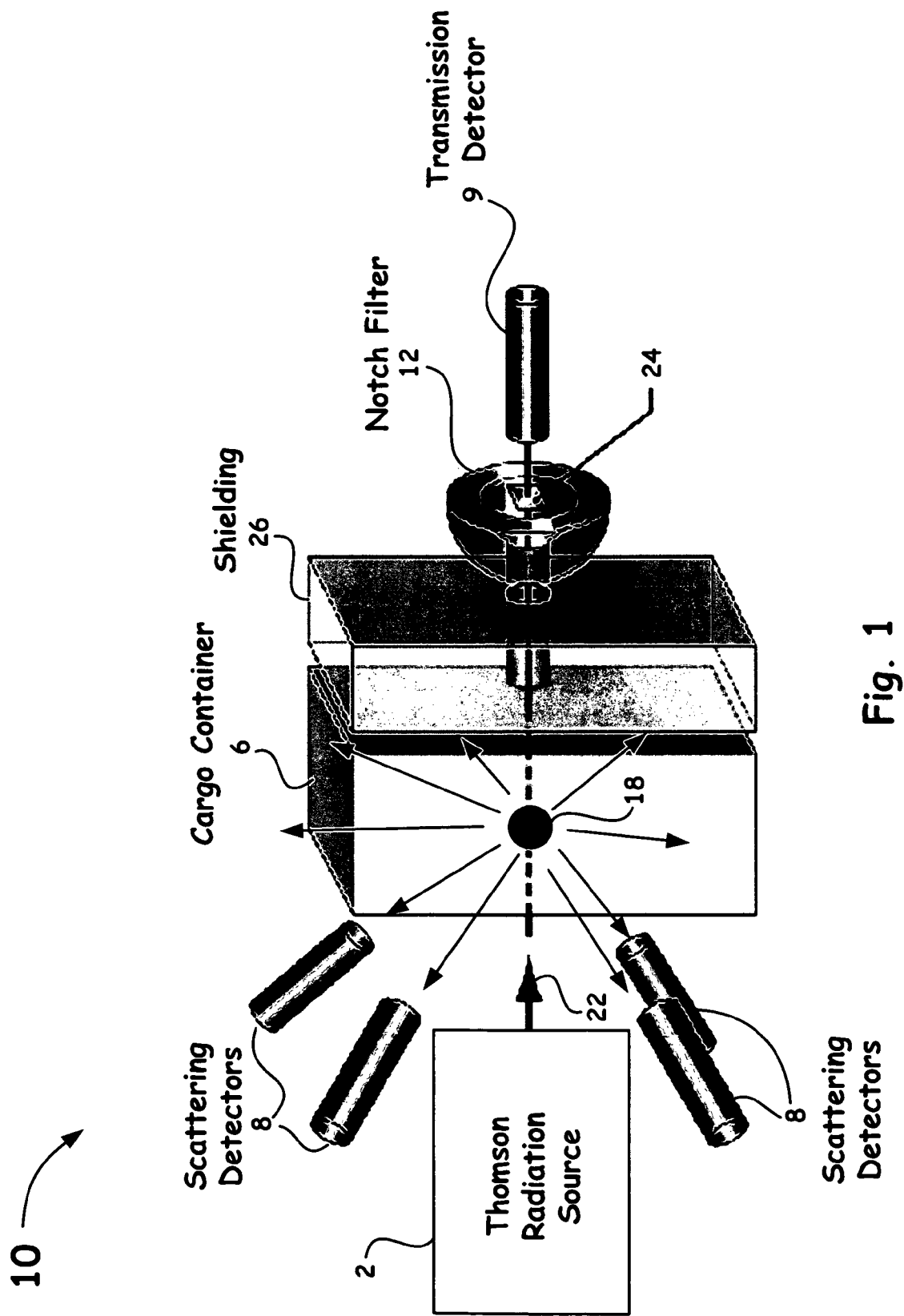
FIG. 1 shows a basic schematic representation of a Nuclear resonance Fluorescence (NRF) based interrogation system of the present invention.

Referring now to the drawings, specific embodiments of the invention are shown. The detailed description of the specific embodiments, together with the general description of the invention, serves to explain the principles of the invention.

Unless otherwise indicated, all numbers expressing quantities of ingredients, constituents, reaction conditions and so forth used in the specification and claims are to be understood as being modified in all instances by the term "about". Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical value, however, inherently contain certain errors necessarily resulting from the standard deviation found in their respective testing measurements.

General Description

The detection scheme and apparatus, as disclosed herein, is based on high-energy x-ray excitation and monitoring of nuclear resonance fluorescence (NRF) from target nuclei. The implementation of NRF-based detection for the present invention depends strongly on the nature of the illumination source, such as a gamma-ray source. The x-ray sources utilized herein are based on Thomson or inverse-Compton scattering of laser photons from beams of relativistic electrons having a narrow relative kinetic energy spread, $\Delta\gamma/\gamma \sim 10^{-3}$, and are quasi-monochromatic (i.e., a fractional bandwidth of about $10^{-3}$), highly collimated (less than about a 1 mrad divergence) and have been shown to scale in spectral brightness as the square of the x-ray energy. Using the methods and apparatus of the present invention, a relatively compact T-REX (Thomson-Radiated Extreme X-ray) source having dimensions of about 3 m to about 10 m can be configured to produce tunable pulses of narrow-bandwidth photons from about the 10-keV up to about the 5 MeV range with a peak brightness of up to about 15 orders of magnitude beyond that currently available from the world's best synchrotrons at 1 MeV photon energy.

Specific Description

Turning now to the drawings, FIG. 1 shows a basic representation of the present invention, generally designated as reference numeral 10. Such a beneficial arrangement includes a Thomson-Radiation source 2 arranged to scan a desired target area (e.g., a cargo container 6), and one or more scattering 8 and/or transmission detectors 9 configured with, for example, a notch filter 12 to provide the sensitivity for detecting and/or imaging any nuclear fluorescence (shown denoted by directional arrows within cargo container 6) that are induced in a material of interest 18 by source 2.

Interrogation with the present invention is accomplished by using photons to resonantly excite electromagnetic transitions in the nuclei of the material 18 of interest. In the example arrangement of FIG. 1, narrowly collimated pulses (i.e., less than about 1 mrad of divergence) of photons are sent to interrogate cargo container 6. The source 2 is tuned so that some fraction of the photons ($\approx 10^{-3}$) has the right energy to excite a resonance in the material 18 of interest (e.g., $^{235}$U). Tuning of the source 2 can be accomplished by, in addition to changing the electron beam energy, changing the interaction laser wavelengths used in the system, such as, by using different lasing materials, lasing modes, or by incorporating, for example, an optical parametric oscillator that can be scanned over a variety of wavelengths. The photon beam is thereafter measured after it exits the container for analysis.

Imaging can be obtained by moving the Thomson-Radiation source 2 or the material 18 (i.e., the cargo container 6). As a novel method of scanning, the beam can be manipulated by carefully controlling the angular distribution of the electrons in the interaction region, e.g., by interacting a trapped laser pulse repeatedly with a series of electron bunches at different space-time locations to produce a series of collimated γ-ray flashes propagating at different angles.

Figure 2B:
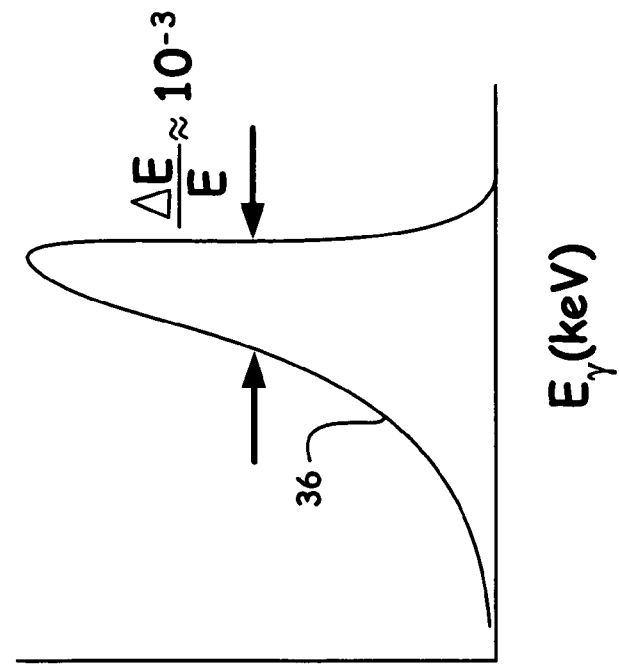
FIG. 2(b) shows a detected spectrum corresponding to a probed area that does not contain a suspect material resulting in a smooth attenuation characteristic of Compton scattering.
Figure 2A:
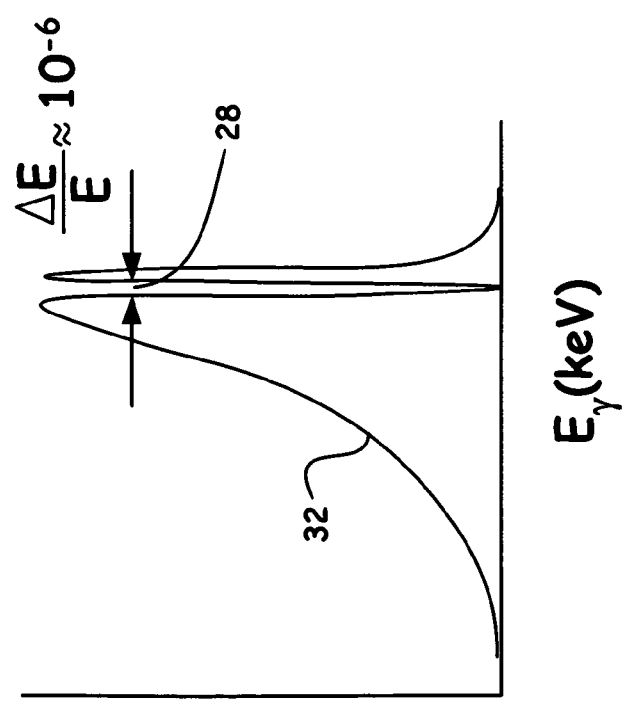
FIG. 2(a) shows a detected spectrum of a suspect material resulting in a depletion of photons, or "notch" arising from absorption of resonant photons.

As shown in FIG. 2(a), if a material or characteristic of a material is present, e.g., if cargo container 6, as shown in FIG. 1, contains $^{235}$U, the beam as measured by transmission detector 9, as shown in FIG. 1, is markedly deficient in resonant photons and contains a "notch" 28 in the detected spectrum 32 (e.g., a notch of $\Delta E/E$ of approximately $10^{-6}$). Such a notch 28 arises because cross sections characterizing nuclear electromagnetic transitions are very large ($\approx 300$ barns), about 1000 times larger than the Compton cross section typical of photon-electron scattering. FIG. 2(b) shows that if the suspected material is not present in the container, the detected signal reveals a smoothly varying attenuation 36 characteristic of Compton scattering.

Returning to FIG. 1, the detection scheme of the present invention utilizes a physical process that is sensitive to the resonant photons. Such a scheme is accomplished by utilizing a shield 26 to prevent detection of background scattered photons, such as atomic processes that include Compton scattered photons, and by placing a small resonant scatterer 24 in front of the beam exiting cargo container 6, which is designed to be of the same nuclear species of interest of the material 18. The detector array 8 measures the rate of resonant scattering and determines the flux of resonant photons exiting cargo container 6. The flux of off-resonant photons is often measured with a simple transmission detector 9, such as, an Aluminum Antimonide radiation detector, a Germanium radiation detector, a high-purity Germanium (HPGe) radiation detector, a cryo-cooled Germanium radiation detector, etc., or any radiation detector having the essential capabilities of measuring the photons of the present invention that can be placed directly in the path of the beam.

A disparity between the attenuation measured for resonant and non-resonant photons indicates that the suspected material is present in the cargo. As the beam 22 (shown with a directional arrow) from source 2 passes through the material 18 of interest, photons are resonantly absorbed by the nuclei of the material 18 depending on the quantity being probed. Thus, the intensities of the photons of specific energies transmitted through the target contain information about the nuclear composition of the probed material 18. If the target contains an amount of a nuclear species of interest, photons of energies corresponding to that quantity of nuclear species are resonantly absorbed and do not become incident on the resonance scatterer 24. Accordingly, the signal captured by transmission detector 9 associated with a predetermined resonance scatterer 24 having that nuclear species is diminished (i.e., the notch 28, as shown in FIG. 2(a), when the beam 22 produced from source 2 interacts with probed material 18.

Figure 3:
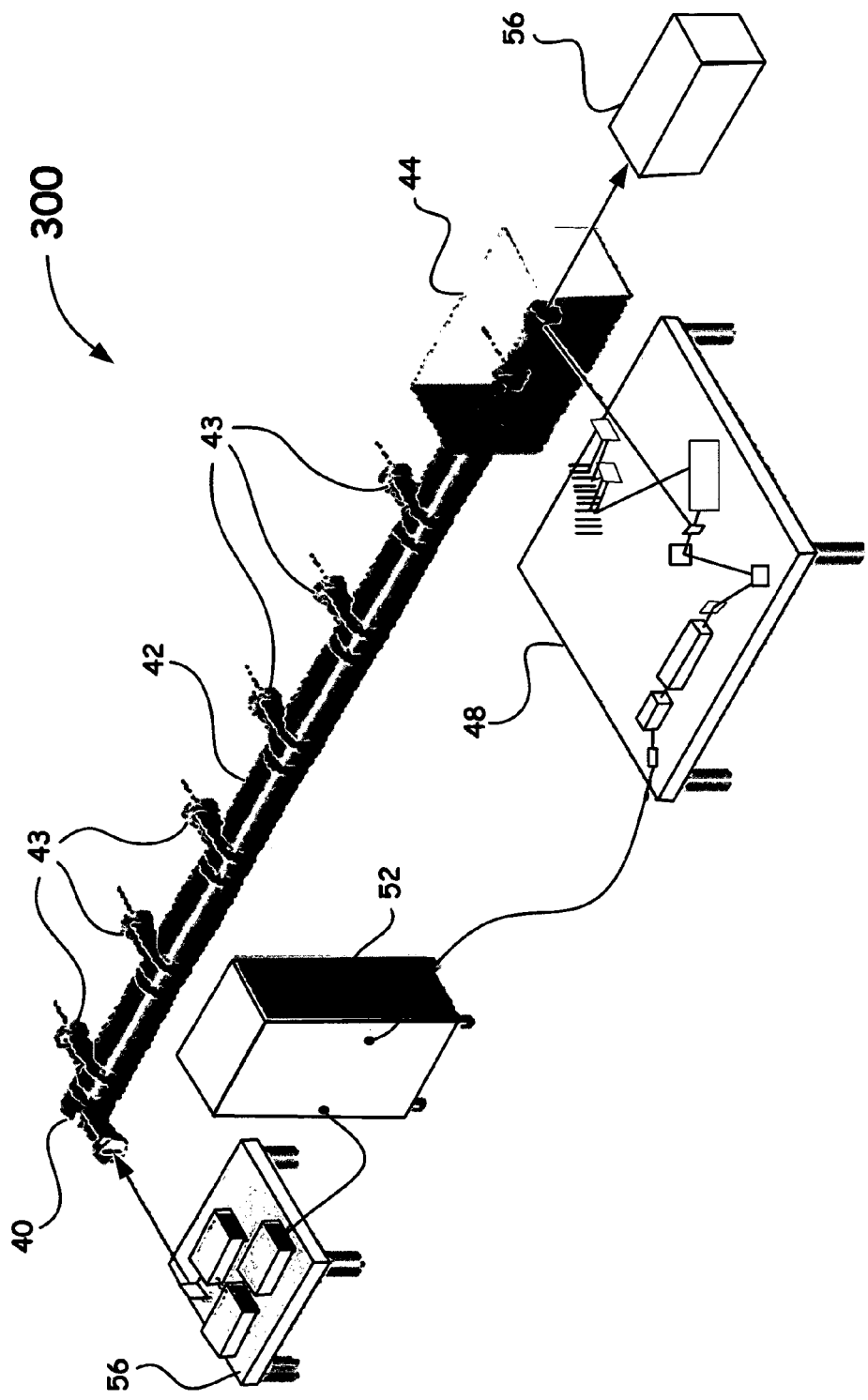
FIG. 3 shows a more detailed representation of a Nuclear resonance Fluorescence (NRF) based interrogation system of the present invention, including the main components of the monochromatic, tunable Thomson x/gamma-ray source.

FIG. 3 shows a more detailed representation of the system, generally designated as reference numeral 300, of the present invention, and includes an RF photocathode gun 40, a linear accelerator 42, an interaction region 44, an interaction laser system 48, a fiber optics rack 52, a photo-cathode driver system 56, and the detector configuration 58, as shown and discussed above in FIG. 1. Each of the sub-assemblies are discussed below in greater detail.

The electron source of the present invention utilizes a 1.6 cell RF photo-cathode gun based design known by those of ordinary skill in the art. The RF gun 40, as shown in FIG. 3, designed and built in collaboration with UCLA is an improved apparatus because of symmetrization and suppression of a parasitic field mode. Frequency tuners in previous versions of such a gun design caused breakdowns at field strengths above 100 MV/m. These tuners have been removed, and are replaced by symmetrizing slots (not shown) identical to the RF input and vacuum pump-out slots. This measure allows peak field strengths of up to about 120 Mv/m, necessary for high-brightness performance. Additional symmetrizing measures include the removal of off-axis laser input ports (not shown), and the inclusion of a corrector coil (not shown), which compensates for dipole and quadrupole moments of the main focusing solenoid.

The gun 40, as shown in FIG. 3, as an RF system that includes two coupled cavities, has two resonant modes, the accelerating, or π-mode, and the parasitic 0-mode. The excitation of the O-mode can have a detrimental effect on the emittance and energy spread of the generated electron beam. The present invention provides a solution to this problem by increasing the frequency separation between the 0 and π-modes, thereby decreasing the amount of 0-mode excitation that occurs in normal operation, which has increased the mode separation from about 3.5 MHz to about 12 MHz. Such a design has been modeled with an emittance as low as about 0.6 mm-mrad rms for a 1 nC bunch.

Electron Beamline Design

The present invention utilizes a linear accelerator (linac), i.e., reference numeral 42 as shown in FIG. 3, having quadrupoles 43 located between accelerating sections in order to transport and accelerate the low emittance electron bunch produced by the gun without significant degradation in beam quality. With such an approach, a normalized emittance as low as about $\epsilon_n$=0.7 (0.95) mm.mrad at 1 nC of bunch charge is achievable at the interaction point; wherein the $2^{nd}$ number (i.e., 0.95) includes thermal emittance. This is to be appreciated by those of ordinary skill in the art because the x-ray brightness has been shown to scale as $\epsilon_n^{-2}$.

One of the major challenges in generating electron bunches with the lowest possible emittance in a high-gradient photoinjector is to produce the optimal spatial and temporal shape for the photocathode drive laser pulse. At S-band, for high-charge operation in the 1 nC range, the target pulse shape is a uniform cylinder of photons, approximately 2 mm in diameter and 10 ps in duration. Such pulses are very difficult to generate, especially at ultraviolet (UV) wavelengths, and this has remained an unsolved issue in rf gun development. The present invention addresses this issue while also addressing cost, efficiency, and complexity, by stacking several short pulses in sequence to generate a long, nominally flat pulse, using a hyper-Michelson interferometer. Using such an arrangement and modeling the resulting laser profile, has shown that even with 20% ripple in the generated electron density, the emittance is not significantly degraded. This corresponds to overlapping of laser pulses interfering at intensity levels of ~1%; furthermore, each two successive pulses are polarized orthogonally to reduce coherence and interference effects.

Producing a flat transverse profile can be modeled by simply truncating a Gaussian pulse at different radii, trading laser energy for flatness. Accordingly, modeling shows that truncating the radius to $0.85\sigma_r$ (rms), provides an optimal electron beam, with $\sigma_r$=1.02 mm.

Charge Optimization, NRF Figure of Merit

An important quantity in the interaction region is the optimal electron bunch charge. Higher charge yields more scattered photons, but it also translates into a higher bunch emittance via nonlinear space-charge effects, leading to spectral broadening and increased x-ray divergence. In order to optimize the present invention a figure of merit is obtained:

$$F(n) = \frac{\text{\# photons in resonance}}{(\text{\# total photons on sample})^n}$$

where n depends on the details of the detection geometry, and lies between ¼ and 1/7. A modeling program with different electron bunch charges, and optimized in each case can be beneficially utilized to get the lowest possible emittance at the interaction point. Thermal emittance effects are included to provide a more realistic electron bunch phase space input to the x-ray code. The Thomson scattering process is simulated using, for example, a 1 J, 355 nm, 5 ps Fourier transform-limited laser pulse scaled to match the electron spot size at the interaction point between about 1 μm and up to about 100 μm, but most often at about 10 μm. The x-ray spectra, integrated over a 1 mrad half-angle cone, are then used to calculate F(¼), which shows an optimum electron bunch charge of 1 nC, with fairly flat charge dependence between 500 pC and 1.5 nC when using an interaction point at about 10 μm.

Thermal Emittance

For low charge simulations, thermal emittance becomes an important quantity that must be properly taken into account. Recently, researchers have published detailed theoretical accounts of the processes leading to thermal emittance. The basic model requires that electrons in the metal, with energy E, absorbing a photon with energy hv, have a total energy higher than the total barrier, $E_b=E_f+\Phi_{eff}$, where $E_f$ is the Fermi level of the metal, and $\Phi_{eff}$ is the work function, which include the Schottky effect induced by the rf field. Within this context, energy spread results from the temperature-dependent Fermi-Dirac distribution, while photoemission angles are restricted to $\cos\theta < \sqrt{E_b/(E+h\nu)}$, and the angular probability distribution yields a finite emittance.

In addition, the skin depth for the rf field is much larger than its optical counterpart, leading to a correlated axial momentum distribution for the photoelectrons. These considerations can be used to construct the photoelectron phase space at the cathode plane, which is then loaded into a modeling program for detailed simulations, fully including space charge.

Three-Dimensional Nonlinear Thomson Scattering Code

The present invention requires desired narrow-band x-rays (e.g. NRF~$10^{-6}$); therefore, broadening mechanisms play a key role in the system performance and require careful modeling. Spectral broadening processes include: laser bandwidth; laser diffraction (effective bandwidth); e-beam energy spread; e-beam emittance; 3D nonlinear effects; radiation reaction (soft recoil); and hard recoil.

The substantially narrow bandwidth of the T-REX drive laser requires precise, advanced sampling techniques capable of spectrally resolving the radiation produced by each individual macro-particle. The fastest and most accurate computer algorithm for this task is a Fast Fourier Transform (FFT) subroutine, which requires that the independent variable be the detector time. The strategy is to use a $4^{th}$-order Runge-Kutta algorithm over $2^n$ steps in the detector time, which then feeds an FFT subroutine to produce the maximum spectral information available from the code. The fully three-dimensional electromagnetic field components are derived from a paraxial generating function that satisfies the Lorentz gauge condition exactly.

The number of photons per unit frequency and per unit solid angle scattered by a single electron and detected at infinity is expressed as:

$$\frac{d^2N}{d\varpi d\Omega} = \frac{\alpha}{4\pi^2\varpi}\left|\int_{-\infty}^{+\infty} e^{i\varpi\bar{t}}\left[n\times(n-\beta)\times\frac{d\beta}{\omega_0 d\bar{t}}(1-\beta\cdot n)^{-3}\right]_{t^-} d\bar{t}\right|^2, \quad (1)$$

where $\alpha$ is the fine structure constant, $\bar{\omega}=\omega/\omega_0$ is the radiation frequency, normalized to the laser frequency, $n=ck/\omega$ is the unit vector in the direction of observation, and where the electron dynamical quantities are evaluated at the retarded time, $t^-=t-r(t^-)/c$; finally, $\bar{t}=\omega_0 t$. Provided that all dynamical quantities are evaluated as functions of the detector time, t, and sampled over $2^n$ constant intervals, Eq. (1) can be calculated using a FFT algorithm.

For a system of n coupled $1^{st}$-order differential equations of the form y'=f(y,t), where y, y'=dy/dt, and f are vector functions with n components, and where t is the independent variable, the $4^{th}$-order Runge-Kutta (RK) algorithm takes the general form:

$$y_{i+1} \cong y_i + \frac{1}{6}(k_1 + 2k_2 + 2k_3 + k_4), \quad (2)$$

where h is the step in the independent variable, and where the recursive evaluations are given by $k_1$=hf($y_i,t_i$), $k_2$=hf ($y_i+k_1/2,t_i+h/2$), $k_3$=hf($y_i+k_2/2,t_i+h/2$), and $k_4$=hf($y_i+k_3,t_i+h$). The $4^{th}$-order RK method converges very fast [o($h^5$)], and considerably reduces the computing time required for tracking a large number of macro-particles.

Three-Dimensional Nonlinear Compton Scattering Theory

While the code presented above is fully three-dimensional, relativistic, and includes nonlinear effects, it does not account for recoil. Two distinct regimes can be modeled: soft recoil, where electrons scatter numerous times off relatively soft photons, as adequately described by the Dirac-Lorentz equation; and hard individual collisions. The $2^{nd}$ type of process is more realistic for T-REX, and can be modeled either via Monte-Carlo methods; or in an average manner, where one takes advantage of the fact that, while each electron scatters only a few times at most, the code follows a large population of electrons, over which averaging is meaningful. An efficient approach is to modify the radiation formula, so that it agrees with the Compton formula for plane waves (photons). The complete derivation is somewhat involved; only the salient step is referenced here. Upon adding a recoil component, $\lambda_c k_\mu^0$, to the Ballistic 4-Velocity, $u_\mu^0$, the radiation formula, $$\frac{d^2N}{d\omega d\Omega} = \frac{\alpha\omega}{4\pi^2}\left|n\times\int_{-\infty}^{+\infty} u(\tau)\exp[-ik_\mu^S x^\mu(\tau)]d\tau\right|^2, \quad (3)$$

yields the Compton formula, $k_\mu^S(u_0^\mu+\lambda_c k_0^\mu)=k_\mu^0 u_0^\mu$. Here, $k_\mu^0$ and $k_\mu^0$ are the incident and scattered 4-wavenumbers, and $x^\mu(\tau)$ is the electron trajectory during the interaction. A generalized form of this modification is used to yield the average recoil-induced spectral broadening for fully three-dimensional, nonlinear interactions.

Seed Laser System (SLS)

Figure 4:
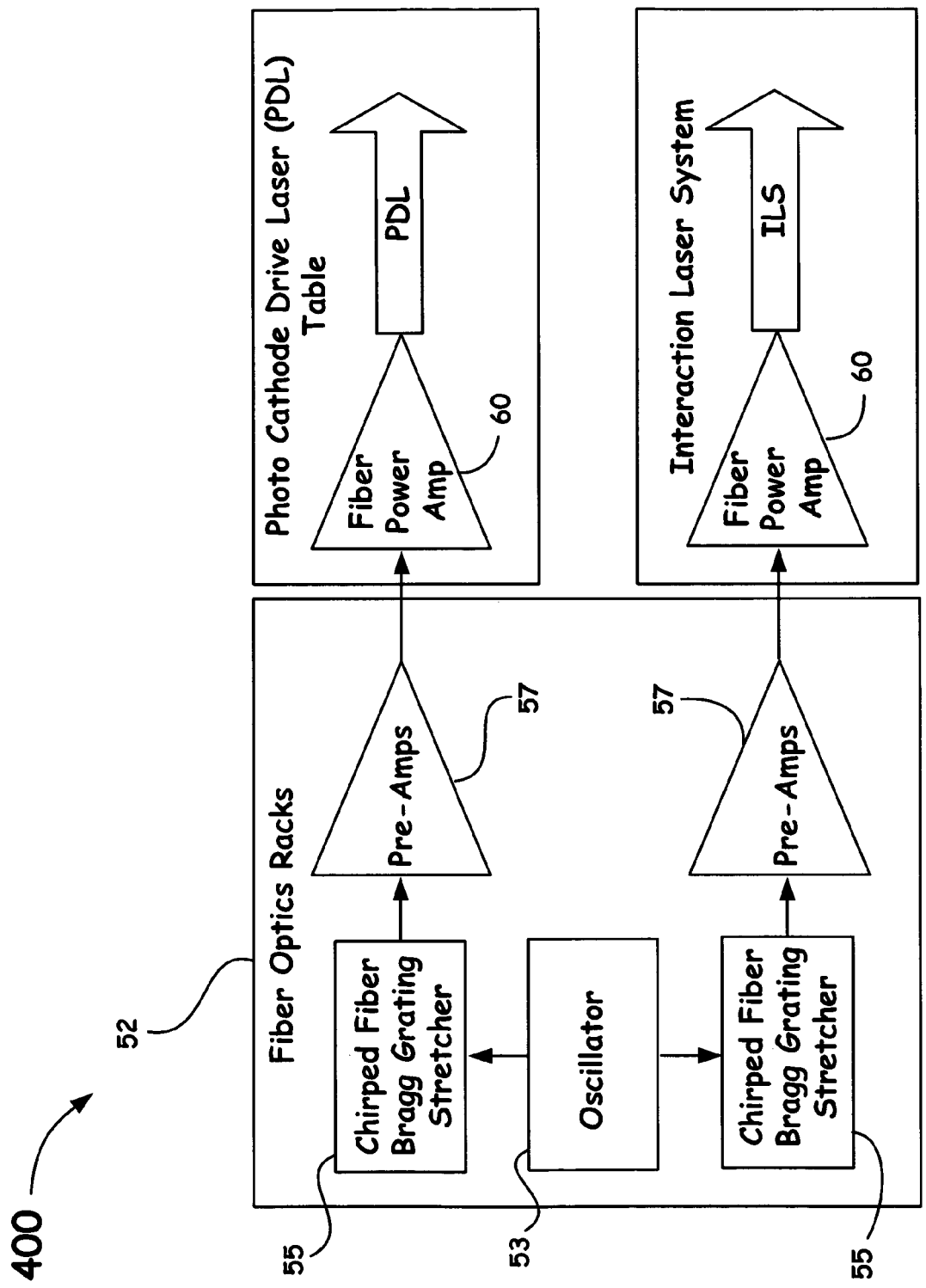
FIG. 4 shows a schematic of the Seed Laser System (SLS).

The Seed Laser System (SLS) is preferably based on optical fiber technologies to make it reliable, robust, and compact. The SLS, as shown in FIG. 4 generally designated by reference 400, is physically divided into three sections, as follows:

A rack-mounted fiber optics unit, 52 as shown in FIG. 3 and in FIG. 4, includes:

A passively mode-locked oscillator 53 that can generate a train of 150 fs pulses locked to a frequency of 40.7785 MHz±1 Hz. The pulse spectrum spans 1040 nm through 1070 nm so this single oscillator can seed both the PDL and the ILS.

A pair 55 of chirped fiber Bragg gratings (CFBG's): one to stretch the PDL pulse train and another to stretch the interaction laser (ILS) train. The CFBG's are double-passed to obtain a total stretch of 6 ns.

Yb-doped fiber pre-amplifiers 57, often six Yb-doped fiber pre-amplifiers: three for the PDL line and three for the ILS line. These raise the pulse energy in each line from roughly about 0.1 nJ at 40 MHz to about 10 nJ at 2 kHz. Each pre-amplifier also contains an isolator (not shown), an acousto-optic modulator (not shown) to clean the pulses in the time domain, and an optical tap (not shown) for monitoring purposes.

A pair of tabletop high-energy amplifiers 60: one for the PDL line and one for the ILS line. The amplifiers often include, but are not limited to:

A section of Yb-doped fiber to convert the output received from the fiber optics rack (e.g., about 10 nJ pulses plus 300 W of pump power at 976 nm) up to about 1 µJ pulses. The conversion is delayed to the table-tops to reduce the nonlinear effects that can accrue during transport from the rack to the tables.

A final amplifier section can raise the pulse energy up to about 1 mJ having phase errors in the spectral components to less than about π/4.

A control and analysis means (not shown), such as, but not limited to, a desktop or laptop computer is often arranged to monitor and control the outputs of the pre-amplifier stages and final amplifier to ensure reliable day-to-day operation and to intervene if one or more of the stages show signs of failure. Such an analysis means can also monitor the frequency and phase of the locking circuitry, and make minor adjustments to beam pointing to adjust for anticipated thermal drifts.

It is to be appreciated that the final amplifier fiber ultimately limits the achievable pulse energy because of inherent nonlinearities and damage threshold. Accordingly, while various amplifier fibers may be incorporated, most often a 40 µm single-mode, single-polarization fiber from Crystal Fibre, or a 30 µm fiber from LIEKKI is integrated into the present invention to provide the desired beam quality and polarization extinction ratio.

Photocathode Drive Laser (PDL)

A PDL 56, as shown in FIG. 3, of the present invention generates the photoinjector drive pulse for the photocathode 40 in the linac photoinjector. The system has been designed to deliver a "beer-can" shaped pulse with energy of up to about 100 µJ at 261.75 nm. The "beer-can" shape (a flattop in both space and time) is 10 ps at FWHM, with ~800 fs rise and fall times. The spot-size diameter of the beam measures 2 mm.

Figure 5:
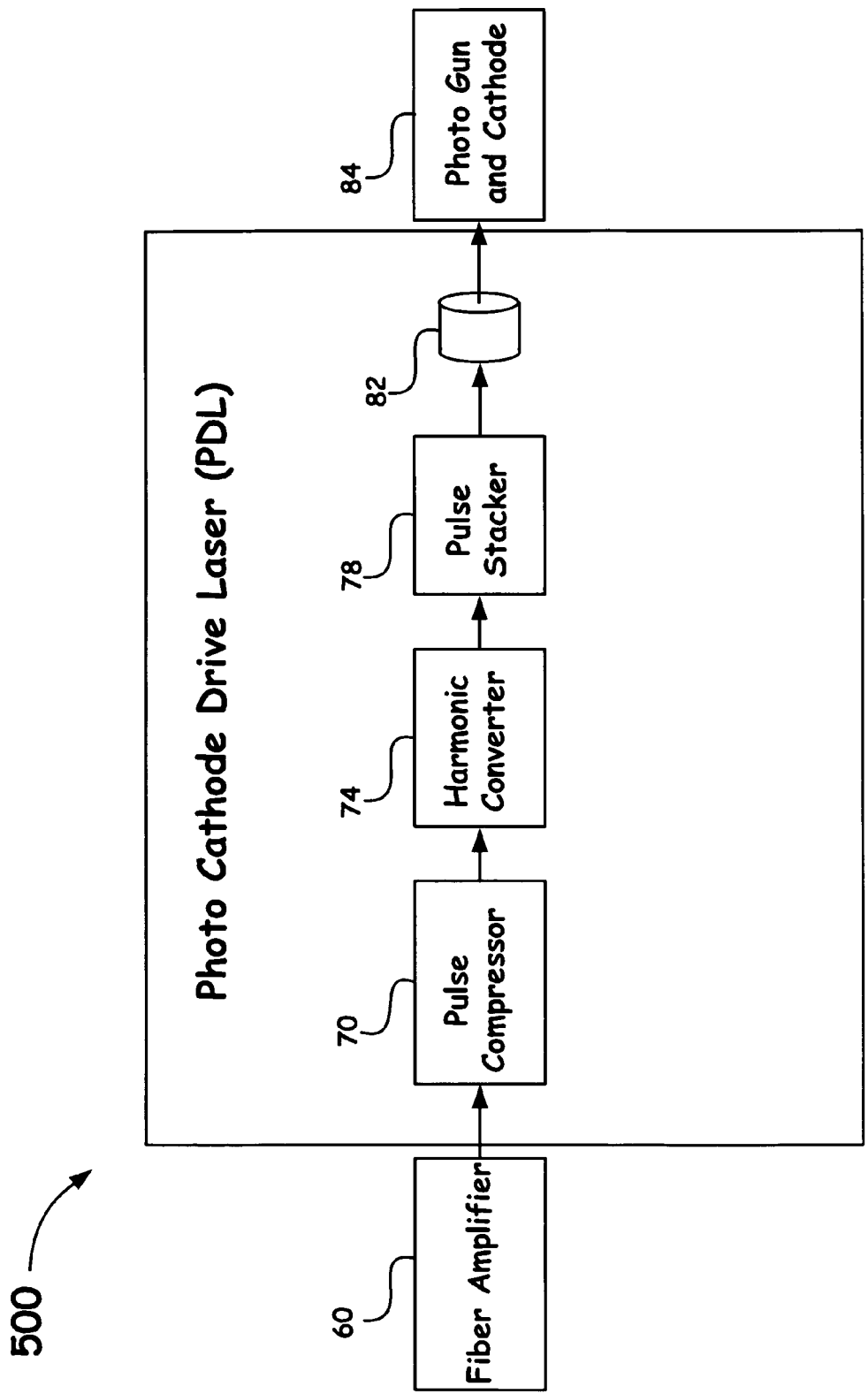
FIG. 5 shows a schematic of the Photocathode Drive Laser (PDL).

The PDL system, generally designated by reference numeral 500, as shown by the schematic representation in FIG. 5, often includes 4 main components: a pulse compressor 70, a harmonic conversion stage 74, a pulse stacker 78, which temporally shapes the UV pulse, and a custom designed phase mask optic 82, which spatially reshapes the Gaussian UV pulse to a substantially flattop profile. An exemplary input to the PDL, generated by the SLS system, upon amplification by Fiber Amplifier 60, is a ~500 µJ pulse at 1047 nm with a ~10 nm bandwidth stretched to ~4.8 ns FWHM.

Compressor 70 compensates for the group delay dispersion (GDD) and third-order dispersion (TOD) introduced in the SLS system while recompressing the input pulse from about 4.8 ns to about 250 fs FWHM. The preferred design is a quad-pass pulse compressor, having a resultant GDD=−3.4× $10^8$ fs$^2$, and TOD=4.7×$10^9$ fs$^3$, and often includes one 1740 groves/mm grating, 1 horizontal roof mirror, 1 large vertical roof mirror, and 1 small vertical roof mirror so as to achieve a dispersion of about 600 ps/nm.

In a further method of the present invention, the compressed pulse is frequency-quadrupled from 1047 nm to 261.75 nm in harmonic converter 74, as shown in FIG. 5. Harmonic conversion occurs in two steps. First, the pulse is frequency-doubled to 523.5 nm with, for example, a BBO crystal in the Type I configuration (crystal cut angle=23.2°, crystal thickness, ~600 µm). The residual 1047 nm beam is then filtered out using a dichroic mirror. The up-converted beam can then be frequency Type I frequency-doubled from 523.5 nm to 261.75 nm by a different BBO crystal. The conversion efficiency from 2ω to 4ω is limited by the 2-photon nonlinear absorption of the UV radiation in the BBO crystal. This constraint is partly overcome by using two 2ω-to-4ω doubling crystals. The first BBO crystal partially depletes the green (523.5 nm) pump. The generated UV beam is then separated out with a dichroic mirror; the residual green beam is sent to a second BBO crystal. The two generated UV beans are later recombined in the pulse stacker. The BBO crystals are chosen thin enough to minimize 2-photon absorption. The first 2ω-to-4ω BBO crystal is ~200 µm thick and the second BBO crystal is ~400 µm thick.

A pulse stacker 78, as shown in FIG. 5, of the present invention is often a Michelson-based ultrafast pulse multiplexing device having nearly 100% throughput and designed for high energy shaped pulse generation. The pulse stacker generates a train of replicas of the input pulse delayed with respect to each other with femtosecond precision. Half of the produced pulses are s-polarized and half are p-polarized. Appropriate setting of the interferometer arm lengths results in many different output pulse formats. The designed pulse stacker can include 4 stages and two input ports (for the two generated UV beams), capable of stacking up to 32 pulses. To create the optimal photo-injection pulse, the two UV input pulses are initially temporally stretched to ~400 fs and then multiplexed with the pulse stacker to create a train of orthogonally polarized pulses spaced by 280 fs, which corresponds to a temporal flattop pulse with 10 ps duration and 1 ps rise time having some minimal temporal modulation caused by pulse interference.

To maximize beam throughput and minimize the footprint of the pulse stretcher, a four-prism set-up can often be utilized. The beam is incident on each of the fused silica prisms at Brewster's angle. A prism pair separation of 50 cm stretches a 250 fs transform-limited pulse to 1.2 ps FWHM.

A custom-designed phase mask optic 82, as shown in FIG. 5, reshapes the input Gaussian pulse to a flattop spatial profile. The optic imparts a spatial phase to the UV beam to produce a flattop pulse in the Fourier plane. The beam shape is preserved by imaging the Fourier plane to the photo-cathode 84, as shown in FIG. 5.

Resizing of the beam waist at the different stages of the PDL system is achieved with an off-axis beam (de-) expander. The beam expander is preferably a concave (R=75 cm) and a convex (R=−50 cm) mirror placed at a slight angle (~0.5 deg) with respect to each other. This design eliminates any astigmatism introduced by a conventional on-axis mirror expander.

The designed PDL system can be made to fit on a 2'×8' optical board, so as to be placed next to the linac photoinjector approximately 2 m from the photocathode. The beam then can be imaged from the optical board layout to the photocathode.

Interaction Laser System (ILS)

The purpose of the Interaction Laser System 48, as shown in FIG. 3, is to deliver Joule-class 355-nm pulses (the third harmonic of Nd:YAG) to the interaction region 44 at up to about a 10-Hz rate, synchronous with the photoinjector and linac 42. While Nd;YAG is a beneficial laser and amplifier material, other laser materials, such as, but not limited to, Yb:YAG, Nd:YLF, Neodymium(Nd)-doped glass, Yb:YAG, Ti:Sapphire, Yb:glass, KGW, KYW, YLF, S-FAP, YALO, YCOB, Cr:forsterite, and GdCOB and associated amplifying hardware can also be utilized in the present invention without departing from the spirit and scope of the present invention.

It is to be appreciated that the nominally picosecond duration achievable with Nd:YAG (limited by the available gain bandwidth) includes a seed source phase locked to the photocathode drive laser (PDL) 56, as shown in FIG. 3, a multi-head Nd:YAG power amplifier, and a unique hyper-dispersion pulse compressor.

ILS Seed Source

The seed laser system includes a fiber-based system designed to deliver 1064-nm seed pulses temporally stretched to 6-ns duration in a double-passed chirped-fiber Bragg grating. These pulses are amplified to the mJ level in a multi-stage fiber amplifier, at which point they are available to be injected in the ILS power amplifier. Though amplification in Nd:YAG will naturally limit the bandwidth of the energetic output pulses, the ILS seed pulses are amplified with a 1 to 2 nm FWHM bandwidth in order to spectrally fill the available gain spectrum.

ILS Power Amplifier

The nominally 6-ns long 1064-nm pulses supplied by one arm of the SLS are quite similar to the seed pulses used in commercial Q-Switched Nd:YAG lasers. Such lasers are typically limited to less than a handful of longitudinal modes as opposed to the wide-spectrum chirped pulses we will use. As long as the bandwidth of the seed pulses is on the order of the available gain bandwidth, stock Nd:YAG amplifiers from a commercial vendor can be used to boost the mJ-level output of the SLS fiber amplifiers to the Joule-level. This is indeed the path being taken for the ILS amplifier. The design can be arranged with three commercial flashlamp-pumped Nd:YAG laser heads: a 4-pass 6-mm and two 12-mm single-pass rods in a birefringence compensating configuration, with an estimated 3-J output energy.

Hyper-Dispersion Compressor

Chirped-pulse amplification in Nd:YAG with nanometer bandwidths requires a cascaded-grating "hyper-dispersion" architecture to provide the necessary dispersion (~3000 ps/nm) in a compact meter-scale compressor. The design, as disclosed herein, uses four multi-layer diffraction (MLD) diffraction gratings in a double-pass configuration (eight grating reflections in total), however by utilizing appropriate folding of the beam path only a single large-area (35-cm×15-cm, 1740 g/mm) grating is required. A detailed discussion of related hyper dispersion architectures and methods can be found in Incorporated by reference Co-pending, Co-filed U.S. application Ser. No. 11/166,988, filed Jun. 23, 2005, titled "HYPER DISPERSION PULSE COMPRESSOR FOR CHIRPED PULSE AMPLIFICATION SYSTEMS" by Barty, and assigned to the assignee of the present invention, the disclosure of which is herein incorporated by reference in its entirety.

Inverse Density Radiography

An example novel method application of the present invention is directed to the inverse problem of detecting a light thin object inside an optically thick container. Conventionally, a difficulty arises because light elements do not have strong absorption cross sections for x-rays. The other part of the difficulty can be understood quantitatively by considering the signal to noise ratio characterizing detection. If $\tau_{container}$ represents the optical depth of the container to interrogating photons, and $\tau_{object}$ the optical depth of the enclosed object, then the signal to noise ratio scales as $$\frac{S}{N} = \exp[-\tau_{container}] \times (1 - \exp[-\tau_{object}]).$$

Figure 6A:
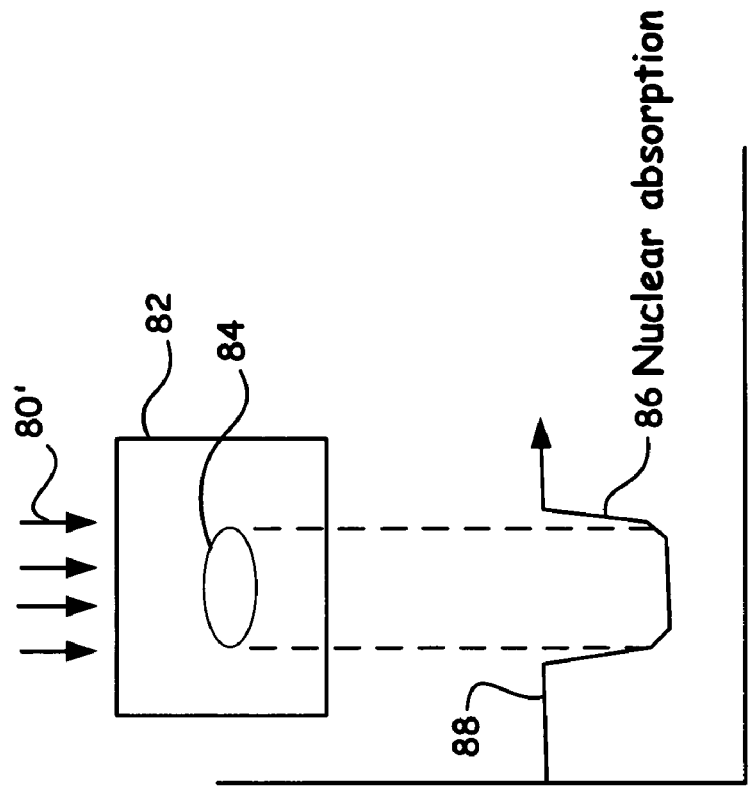
FIG. 6(a) shows imaging of a light object enclosed in a container using conventional atomic radiography.
Figure 6A:
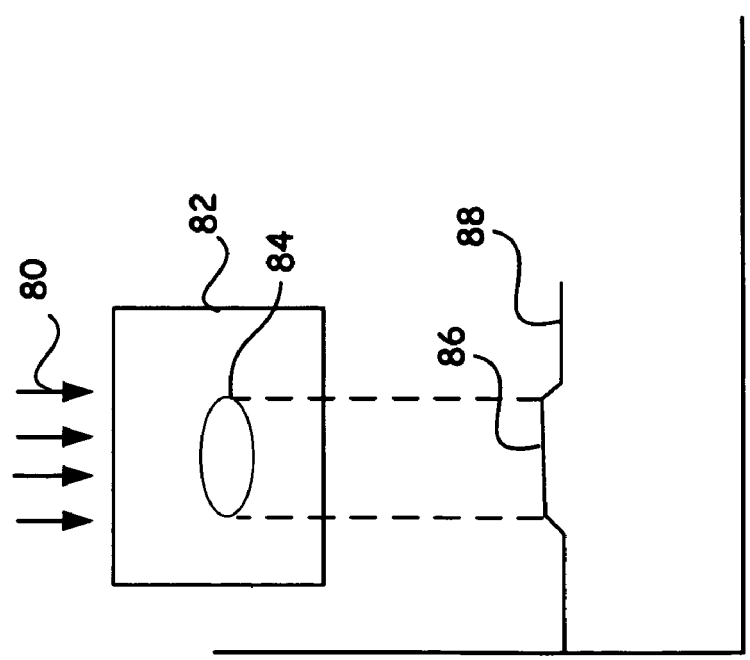

For large container optical depths or small object optical depths the signal to noise ratio approaches zero. FIG. 6(a) graphically illustrates the difficulty wherein a beam 80 (denoted with directional arrows) of conventional technology transmitted through a thick material 82 (e.g., lead) having an enclosed light thin object 84 (e.g., $^7$Li). As shown in FIG. 6(a) the desired detection signal 86 upon collection can be almost undetectable in the overall detected signal 88.

Isotope specific imaging with the methods and apparatus of the present invention address this difficulty by tuning the light source energy to coincide with a strong resonance in the isotope suspected of being inside the container. Because the cross section for resonant nuclear absorption can be large compared to atomic cross sections, the enclosed object appears very thick to resonant photons as utilized herein. The signal to noise ratio for NRF-based imaging of the object becomes:

$$\frac{S}{N} = \exp[-\tau_{container}] \times (1 - \exp[-\tau_{nuclear}]),$$

where $\tau_{nuclear}$ is the optical depth of the object to resonant processes and is large for strong resonances. FIG. 2(b) illustrates detection when NRF using a beam 80' (again shown with directional arrows) and methods as disclosed herein is used. As illustrated, since the enclosed object, such as, a light thin object 84 within a thick object 82 poses a very large optical depth to the directed resonant photons, the signal to noise ratio greatly improves to enable detection of signal 86 that is contrasting with the signal 88 resulting from other nuclear processes.

Nuclear Spectroscopy with Polarized, Monochromatic Light

The present invention includes improving the understanding of nuclear level densities and the rich variety of collective motion that can occur in nuclei. Sources of the present invention can probe specific levels, one at a time. Many other nuclear probes result in signals that are more complicated to de-convolve. Combined with 100% polarization, measurements using the present invention improve upon the determination of the electromagnetic character of excited levels. Applications include establishing the extent to which nuclei exhibit "mixed symmetry" collective motion, and the role that such modes play in so-called pygmy dipole resonances.

Waste Analysis

The present invention, as an isotopic-specific detection technology, also represents a means for large-scale screening of stored waste to account for rapid identification and segregation of stored waste by isotopic interrogation, as well as reduction of waste-storage overhead. With 3D imaging, non-destructive evaluation of the contents of a storage vessel can be made without opening or disturbing the contents so as to provide an important measure of safety in the handling of such wastes.

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The invention claimed is:

1. A Nuclear Resonance Fluorescence detection method, comprising:
   directing a beam of Thomson radiation comprising a fractional bandwidth of about $10^{-3}$ at a target region so as to probe for one or more suspect materials;
   resonantly exciting nuclei of said one or more suspect materials within said target region with said beam of Thomson radiation;
   resonantly exciting nuclei of a reference scatterer with said beam transmitted through said suspect material, said reference scatterer comprising one or more predetermined nuclear species of interest; and
   measuring an energy spectrum of photons resulting from said resonantly excited reference scatterer, wherein a disparity between the attenuation measured for resonant and non-resonant photons indicates a detected said suspect material.

2. The method of claim 1, wherein said beam of Thomson radiation comprises a beam diameter from about 1 micron to about 100 microns.

3. The method of claim 2, wherein said beam of Thomson radiation comprises a beam diameter of about 10 microns.

4. The method of claim 1, wherein said beam of Thomson radiation comprises beams of relativistic electrons having a narrow relative kinetic energy spread, $\Delta\gamma/\gamma$ of less than about $10^{-3}$.

5. The method of claim 1, wherein said measured disparity between resonant and non-resonant photons comprises an attenuation width, $\Delta E/E$, of less than about $10^{-6}$.

6. The method of claim 1, wherein said beam of Thomson radiation comprises a beam divergence of less than about 1 mrad.

7. The method of claim 1, wherein a detector array is configured to measure the rate of resonant scattering so as to determine the flux of resonant photons exiting said target region.

8. The method of claim 1, wherein said target having said suspect material is imaged by moving the beam, the target, or both, and/or by controlling the angular distribution of the electrons in the interaction region of said Thomson radiation source so as to scan said beam over the extent of said target.

9. The method of claim 1, wherein said Thomson radiation can be tuned to a resonant energy by changing the electron beam energy or by changing the laser interaction wavelengths.

10. A Nuclear Resonance Fluorescence apparatus, comprising:
a Thomson radiation source comprising a fractional bandwidth of about $10^{-3}$;
means for directing said Thomson radiation source at a target region;
one or more reference resonance scatterers, said reference resonance scatterers comprising one or more predetermined nuclear species of interest and wherein said one or more reference resonance scatterers are further configured to receive transmitted radiation resulting from said Thomson radiation source through said target; and
means for measuring a predetermined nuclear species of interest by measuring the energies of photons scattered from said reference scatterers, wherein a disparity between the attenuation measured for resonant and non-resonant photons indicates a detected suspect material.

11. The apparatus of claim 10, wherein said Thomson radiation source comprises a beam diameter from about 1 micron to about 100 microns.

12. The apparatus of claim 11, wherein said Thomson radiation source comprises a beam diameter of about 10 microns.

13. The apparatus of claim 10, wherein said Thomson radiation source comprises relativistic electrons having a narrow relative kinetic energy spread $\Delta\gamma/\gamma$, of less than about $10^{-3}$.

14. The apparatus of claim 10, wherein said measured disparity between resonant and non-resonant photons comprises an attenuation width, $\Delta E/E$, of less than about $10^{-6}$.

15. The apparatus of claim 10, wherein said Thomson radiation source comprises a beam divergence of less than about 1 mrad.

16. The apparatus of claim 10, wherein a detector array is configured to measure the rate of resonant scattering so as to determine the flux of resonant photons exiting said target region.

17. The apparatus of claim 10, wherein said target having said suspect material is imaged by moving the beam, the target, or both, and/or by controlling the angular distribution of the electrons in the interaction region of said Thomson radiation source so as to scan said beam over the extent of said target.

18. The apparatus of claim 10, wherein said Thomson radiation source comprises a resonant energy tuned by changing an electron beam energy or an interaction lasing wavelength so that a predetermined fraction of the photons has the right energy to excite a resonance in a nuclear species of interest.

19. The apparatus of claim 18, wherein said interaction lasing wavelengths are obtained by a lasing material selected from Neodymium(Nd)-doped glass, Neodymium-doped yttrium lithium fluoride, Yb:YAG, Ti:Sapphire, Yb:glass, KGW, KYW, YLF, S-FAP, YALO, YCOB, Cr:forsterite, and GdCOB.

20. The apparatus of claim 18, wherein said interaction lasing wavelengths are obtained by utilizing an optical parametric oscillator.

21. The apparatus of claim 10, wherein said means for measuring comprises at least one detector selected from: an Aluminum Antimonide radiation detector, a Germanium radiation detector, a high-purity Germanium (HPGe) radiation detector, and a cryo-cooled Germanium radiation detector.

* * * * *